United States Patent [19]

Matsuda et al.

[11] 4,436,916

[45] Mar. 13, 1984

[54] PROCESS FOR THE PREPARATION OF INDOLES

[75] Inventors: Fujio Matsuda, Kamakura; Takazo Kato, Ashigarakami; Tadatoshi Honda, Fujisawa; Kazuhiro Terada, Yokohama; Yasuo Kogure, Yokosuka, all of Japan

[73] Assignee: Mitsui Toatsu Chemicals, Inc., Tokyo, Japan

[21] Appl. No.: 264,627

[22] Filed: May 18, 1981

[30] Foreign Application Priority Data

Jun. 3, 1980 [JP] Japan ............................... 55-73741

[51] Int. Cl.$^3$ .................. C07D 209/08; C07D 209/12
[52] U.S. Cl. .................................................. 548/508
[58] Field of Search ..................... 260/319.1; 548/508

[56] References Cited

U.S. PATENT DOCUMENTS 3,699,120 10/1972 Bakke et al. ..................... 260/319.1
3,984,434 10/1976 O'Murchu ....................... 260/319.1

FOREIGN PATENT DOCUMENTS 50-197608  3/1975  Japan ............................... 260/319.1
54-105663  2/1979  Japan ............................... 260/319.1
55-108850  8/1980  Japan ............................... 260/319.1
56-36451   4/1981  Japan ............................... 260/319.1

OTHER PUBLICATIONS

J.A.C.S., Heine et al., "The Synthesis of Some N-Arylethylenimines" 76, 2503, (1954) p. 2503.
Ind. Eng. Chem., Prod. Res. Dev., vol. 15, No. 3, 1976, Bhattacharyya and Nandi, "Synthesis of N-N-Dimethylaniline from Aniline and Methanol", pp. 201–206.
Chemical Abstracts, 66, 75974s, (1967), pp. 7126–7127.
Chemical Abstracts, 70, 78437n, (1969), p. 6.
Ind. Eng. Chem. 43(7), 1579, (1951), Catalytic Reactions of Aromatic Amines, Alkylation with Alcohols, Hill et al.
Chemical Abstracts, 82, P170329z, (1975), Governale et al.
J.A.C.S., 101:2, Jan. 17, 1979, "Reactions of Aniline with Olefins Catalyzed by Group 8 Metal Complexes: N-Alkylation and Heterocycle Formation".
"Classification of Catalysts by Reactions", edited by Tarama Laboratory Staff of Kyoto University, Japan, published by Kagaku Kogyo Sha (Chemical Industrial Co.) of Tokyo Japan, pp. 74–76, (Sep. 1, 1971).

*Primary Examiner*—Paul M. Coughlan, Jr.
*Assistant Examiner*—D. B. Springer
*Attorney, Agent, or Firm*—Fisher, Christen, & Sabol

[57] ABSTRACT

A process for the preparation of indole and derivatives thereof wherein an aniline is reacted with a 1,2-glycol in the vapor phase, the liquid phase or a mixed vapor-liquid phase. A sulfide or selenide or cadmium and/or zinc are used as the catalyst for this reaction. The present invention makes it possible to prepare indole and derivatives thereof in a single step by using inexpensive compounds as the starting materials.

10 Claims, No Drawings

PROCESS FOR THE PREPARATION OF INDOLES

BACKGROUND OF THE INVENTION (1) Field of the Invention

This invention relates to a process for the preparation of indole and derivatives thereof by reacting an aniline with a 1,2-glycol in the presence of a catalyst containing a sulfide or selenide of cadmium and/or zinc.

(2) Description of the Prior Art

In the prior art, indole derivatives have long been prepared by the well-known Fischer indole synthesis in which phenylhydrazine is reacted with a compound having an aldehyde group. If the aldehyde compound is other than acetaldehyde, the aforesaid Fischer indole synthesis can be applied to obtain indole derivatives in good yield. However, if the aldehyde compound is acetaldehyde, no reaction that yields indole has been believed to take place. In order to overcome this disadvantage, there has recently been proposed an improved process which comprises reacting phenylhydrazine with acetaldehyde at an elevated temperature of from 300° to 400° C. in the presence of an alumina catalyst (Japanese Patent Laid-Open No. 76864/1973).

This process surely permits the reaction to proceed and brings about the formation of indole, but fails to give a satisfactory yield. Moreover, it is greatly disadvantageous in that the catalyst has so short a life as to become totally inactive after 0.5–1 hour's use.

Indole can also be prepared by another process which comprises reacting o-toluidine with formic acid to form o-methyl-N-formylaniline and then fusing it together with potassium hydroxide. However, it is usually impossible to selectively prepare o-toluidine that is used as the starting material in this process. That is, the p-isomer is always formed in an amount equal to or greater than that of the o-isomer. Thus, treatment of the isomer formed as a by-product poses a serious problem in the case of industrial production. Moreover, the handling of solids as in alkali fusion is troublesome. For these reasons, the aforesaid process cannot be regarded as suitable for industrial purposes.

Furthermore, a number of attempts have been made to synthesize indole from N-β-hydroxyethylamine, but none of them are satisfactory from an industrial point of view. For example, a process which comprises effecting the reaction at 300° C. in the presence of an aluminosilicate catalyst [Zhur. Obschue. Khim., Vol. 24, pp. 671–678 (1954)] gives only a very low yield of indole. A process which comprises heating the reactant together with a molten mixed salt consisting mainly of zinc chloride (Japanese Patent Laid-Open No. 57968/1973) can give a fairly high yield of indole. However, this process has the disadvantage of requiring a complicated procedure, which makes it unsuitable for industrial purposes.

As described above, a number of processes for the synthesis of indole and derivatives thereof have been proposed. However, many of them are disadvantageous in that large amounts of by-products are formed, expensive compounds are used as the starting materials, and/or lengthy and complicated procedures are required to obtain the desired products.

SUMMARY OF THE INVENTION

It is an object of the present invention to provide a one-step process for the highly selective preparation of indole and derivatives thereof by using inexpensive compounds as the starting materials.

According to the present invention, there is provided a process for the preparation of indole and derivatives thereof which comprises reacting an aniline with a 1,2-glycol in the presence of a catalyst containing a sulfide or selenide of cadmium and/or zinc.

This reaction can be carried out both in the liquid phase and in the vapor phase. By way of example, the process of the present invention makes it possible to obtain indole by reacting aniline with ethylene glycol and to obtain 5-methylindole by reacting p-toluidine with ethylene glycol.

Thus, the process of the present invention has a number of advantages. First, the anilines and 1,2-glycols which can be used as the starting materials are very inexpensive. Secondly, the preparation of indole or a derivative thereof from the starting materials can be achieved in a single step. Thirdly, by-products are scarcely formed and a very high selectivity is attained, so that indole or a derivative thereof can be obtained in highly pure form.

DETAILED DESCRIPTION OF THE INVENTION

The aniline used in the process of the present invention is a compound of the general formula

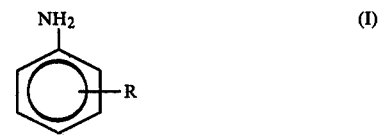

where R represents a hydrogen atom, halogen atom, hydroxyl group, alkyl group or alkoxy group. Specific examples thereof are aniline, o-toluidine, m-toluidine, p-toluidine, o-haloanilines, p-haloanilines, m-haloanilines, o-aminophenol, m-aminophenol, p-aminophenol, o-anisidine, m-anisidine, p-anisidine and the like.

The 1,2-glycol used in the process of the present invention is a number selected from the group consisting of ethylene glycol, propylene glycol, 1,2-butanediol, 1,2,4-butanetriol, glycerol, 2,3-butanediol, diethylene glycol and the like.

The process of the present invention is carried out in the presence of a catalyst. The catalyst used therein is one containing a sulfide or selenide of cadmiun and/or zinc (hereinafter referred to as principal catalytic substances).

These principal catalytic substances may be in any desired forms such as powder, granules, masses, flakes, shaped pieces and the like. Moreover, they may be supported on a carrier together with other compounds, if necessary.

The other compounds which can be used in combination with the principal catalytic substances include the halides, nitrates, sulfates, carbonates, organic acid salts, oxides, hydroxides and the like of lithium, sodium, potassium, magnesium, calcium, strontium, barium, copper, silver, mercury, aluminum, tin, iron, nickel, chromium, manganese, lead, molybdenum and the like; these metals in the elemental state; and the oxides and hydroxides of the constituent metals of principal catalytic substances.

Although any carriers that are in common use for supported catalysts can be used, diatomaceous earth, pumice, titania, silica-alumina, alumina, magnesia, silica gel, activated carbon, activated clay, asbestos and the like are used in typical cases. Supported catalysts can be prepared by supporting the above-described principal catalytic substances on these carriers according to any conventional techniques. For example, a supported catalyst is obtained by soaking a carrier in an aqueous solution containing a water soluble salt of the principal constituent element and adding sodium sulfide or potassium selenide and then drying the carrier until the water included therein is evaporated completely. No particular limitation is placed on the amount of principal catalytic substance supported on the carrier. Usually, depending on the type of carrier used, any suitable amount (for example, from 1 to 50%) of principal catalytic substance may be supported thereon.

Although the process of the present invention can be carried out in the vapor phase, the liquid phase or a mixed vapor-liquid phase, it is usually carried out in the vapor phase. Where the process of the present invention is carried out in the vapor phase, a fixed-bed, fluidized-bed or moving-bed reactor can be used to effect the reaction by heating the vapors of an aniline and a 1,2-glycol in the presence of a catalyst. In this case, various inert gaseous substances may coexist as diluents for the vapors of the starting materials. The useful inert gaseous substances include, for example, nitrogen gas, carbon dioxide gas, water vapor, and the vapors of compounds that are inert to this reaction. Moreover, hydrogen gas or a hydrogen-containing gas is especially suitable for the purpose of maintaining the activity of the catalyst.

Similarly, owing to its ability to suppress the decomposition of the 1,2-glycol over the catalyst, the use of water vapor is suitable for the purpose of maintaining the activity of the catalyst and enhancing the yield of the desired product.

The amounts of aniline and 1,2-glycol fed to the reactor should be such that from 0.01 to 5 moles and preferably from 0.05 to 2 moles of the 1,2-glycol is provided for each mole of the aniline. If the amounts are outside this range, a reduction in yield will be caused and/or large amounts of by-products will be formed. These starting materials are fed, after being vaporized in advance or directly in liquid form, to the reactor at a liquid space velocity of from 0.01 to 5 liters/liter of the catalyst/hour.

The process of the present invention is carried out at a reaction temperature in the range of from 200° C. to 600° C. and preferably from 250° C. to 500° C. If the reaction temperature is lower than 200° C., the reaction can hardly proceed, while if it is higher than 600° C., undesirably large amounts of by-products will be formed.

The reaction pressure may be superatmospheric, atmospheric or subatmospheric.

Where the process of the present invention is carried out in the liquid phase or a mixed vapor-liquid phase, the reaction is effected by heating a mixture of an aniline and a 1,2-glycol in the presence of at least one member selected from the above-described catalysts. In this case, various inert gaseous substances and/or solvents may coexist as diluents for the starting materials. The useful inert gaseous substances include, for example, nitrogen gas, carbon dioxide gas, water vapor and the vapors of compounds that are inert to this reaction. The useful solvents include, for example, benzene, toluene, xylene, methanol, ethanol, isopropanol, dioxane, dimethylformamide, dimethylsulfoxide, pyridine, N-methylpyrrolidone, trimethylamine, diethylamine, triethylamine, tripropylamine, tributylamine, diphenylamine, triphenylamine and other organic solvents.

In the case of liquid-phase reaction, the process of the present invention can be carried out in a fixed-bed, fluidized-bed or moving-bed reactor or in a rotary or continuous reactor for liquid-phase reactions. However, no particular limitation is placed on the type of reactor used.

The amounts of aniline and 1,2-glycol used as the starting materials for this reaction should be such that from 0.05 to 5 moles and preferably from 0.1 to 2 moles of the 1,2-glycol is provided for each mole of the aniline.

No particular limitation is placed on the amount of catalyst used for this reaction. However, the catalyst is generally used is an amount of from 0.01 to 20 g and preferably from 0.1 to 10 g of the active component thereof per mole of the aniline used as one of the starting materials.

The reaction temperature should be in the range of from 200° to 500° C. and preferably from 250° C. to 400° C. If the reaction temperature is lower than 200° C., the reaction can hardly proceed, while if it is higher than 500° C., undesirably large amounts of by-products will be formed.

The reaction pressure may be superatmospheric or atmospheric.

In various embodiments of the present invention, indole or a derivative thereof can readily be obtained in pure form by isolating it from the reaction product according to any conventional technique such as distillation.

The present invention is further illustrated by the following examples.

EXAMPLE 1

Powdery cadmium sulfide (CdS) was pressed into granular form and dried. A 25-mm flow reactor made of Pyrex glass was packed with 50 ml of the cadmium sulfide. The front end of this reactor was connected with a feed inlet pipe and a gas inlet pipe to form a feed vaporization zone, while the rear end thereof was connected with a receiver by way of air-cooling zone.

In the reaction zone, the internal temperature of the reactor was kept at 325° C. Then, a mixture consisting of 93.1 g (1 mole) of aniline and 6.2 g (0.1 mole) of ethylene glycol was introduced thereinto through the feed inlet pipe at a liquid space velocity of 0.1 liter/liter of the catalyst/hour. At the same time, nitrogen gas at atmospheric pressure was passed therethrough in an amount of 10 moles per mole of the aniline used as one of the starting materials. The reaction product withdrawn from the reactor, condensed and collected in the receiver was analyzed by gas chromatography. Thus, it was found that a yield of 8.1 g of indole was obtained. The conversion and selectivity based on the ethylene glycol were 90.1% and 77.2%, respectively. This indicates that by-products were formed in very small amounts.

EXAMPLES 2 TO 10

Reaction was carried out in the same manner as described in Example 1 except that a variety of catalysts were used in place of the cadmium sulfide. The results thus obtained are summarized in Table 1.

TABLE 1

| Example | Catalyst | Data on Indole (based on ethylene glycol) | | |
|---|---|---|---|---|
| | | Amount (g) | Conversion (%) | Selectivity (%) |
| 2 | CdS—diatomaceous earth (with a CdS content of 20%) | 7.1 | 75.2 | 80.5 |
| 3 | CdS—C (with a CdS content of 10%) | 7.3 | 76.6 | 81.4 |
| 4 | CdS—ZnS (with a ZnS content of 20%) | 7.8 | 80.7 | 82.3 |
| 5 | CdS—SiO$_2$ (with a CdS content of 50%) | 8.3 | 78.6 | 90.2 |
| 6 | ZnS | 7.6 | 81.6 | 79.8 |
| 7 | ZnS—C (with a ZnS content of 20%) | 6.7 | 71.2 | 80.3 |
| 8 | ZnS—CuSO$_4$ (with a ZnS content of 50%) | 6.6 | 70.6 | 80.5 |
| 9 | CdSe | 4.9 | 77.5 | 54.2 |
| 10 | ZnSe | 2.1 | 46.2 | 39.0 |

EXAMPLE 11

Using a reactor similar to that of Example 1, reaction was carried out in the same manner as described in Example 1 except that 123 g (1 mole) of p-anisidine was used in place of the aniline. As a result, a yield of 1.9 g of 5-methoxyindole was obtained. The conversion and selectivity based on the ethylene glycol were 17.3% and 73.6%, respectively.

EXAMPLE 12

The procedure of Example 1 was repeated except that a mixed gas consisting of hydrogen gas and water vapor in molar ratio of 9:1 was used in place of the nitrogen gas. This revealed that the selectivity to indole increased to 91.2%.

What is claimed is:

1. A process for the preparation of indoles of formula I

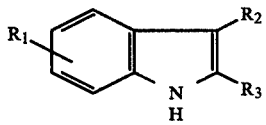

wherein $R_1$ is a hydrogen atom, chlorine atom, bromine atom, methyl group, or methoxy group, and each of $R_2$ and $R_3$ is a hydrogen atom, methyl group or ethyl group, at least one of $R_2$ and $R_3$ is a hydrogen, which comprises the step of reacting a member selected from the group consisting of anilines of formula (II)

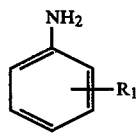

wherein $R_1$ has the same meaning as in the formula I, with a 1,2-glycol selected from the group consisting of ethylene glycol, propylene glycol and 1,2-butanediol in the presence of a catalytic amount of a sulfide or selenide of cadmium and/or zinc in the vapor phase at a temperature of from 200° C. to 600° C., or in the liquid phase or mixed vapor-liquid phase at a temperature of from 200° C. to 500° C.

2. A process as claimed in claim 1, wherein the catalyst is a mixture of cadmium sulfide and zinc sulfide.

3. A process for the preparation of indoles of formula I

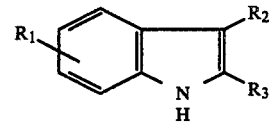

wherein $R_1$ is a hydrogen atom, chlorine atom, bromine atom, methyl group, or methoxy group, each of $R_2$ and $R_3$ is a hydrogen atom, methyl group or ethyl group, at least one of $R_2$ and $R_3$ being hydrogen, which comprises the step of reacting a member selected from the group consisting of anilines of formula (II)

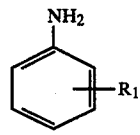

wherein $R_1$ has the same meaning as in the formula I, with a 1,2-glycol selected from the group consisting of ethylene glycol, propylene glycol and 1,2-butanediol in the presence of a catalytic amount of a sulfide or selenide of cadium and/or zinc in the vapor phase at a temperature of from 200° C. to 600° C.

4. A process for the preparation of indoles of formula I

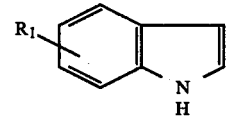

wherein $R_1$ is a hydrogen atom, methyl group or methoxy group, which comprises the step of reacting a member selected from the group consisting of anilines of formula (II)

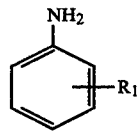

wherein $R_1$ has the same meaning as in the formula I, with ethylene glycol in the presence of a catalytic amount of a sulfide or selenide of cadmium and/or zinc in the vapor phase at a temperature of from 200° C. to 600° C. or in the liquid phase or mixed vapor-liquid phase at a temperature of from 200° C. to 500° C.

5. A process as claimed in claim 4 wherein said member is selected from aniline or p-anisidine.

6. A process as claimed in claim 4 wherein the reaction is carried out in an atmosphere of a mixture of hydrogen gas and water vapor.

7. A process as claimed in claim 4 wherein the reaction is carried out in the presence of water vapor.

8. A process as claimed in claim 4, wherein indole is prepared by the reaction of aniline with ethylene glycol.

9. A process for the preparation of indoles of formula I

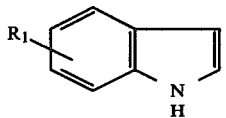

wherein $R_1$ is a hydrogen atom, methyl group or methoxy group, which comprises the step of reacting a member selected from the group consisting of anilines of formula (II)

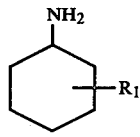

wherein $R_1$ has the same meaning as in the formula I, with ethylene glycol in the presence of a catalytic amount of a sulfide or selenide of cadmium and/or zinc in the vapor phase at a temperature of from 200° C. to 600° C.

10. A process as claimed in claim 9 wherein said member is selected from aniline or p-anisidine.

* * * * *